US00PP10900P

United States Patent [19]

van Andel

[11] Patent Number: Plant 10,900

[45] Date of Patent: May 18, 1999

[54] ALSTROEMERIA PLANT NAMED 'TESTAPINK'

[75] Inventor: Jacob van Andel, Assimeer, Netherlands

[73] Assignee: Van Staaveren b.v., Aalsmeer, Netherlands

[21] Appl. No.: 08/949,973

[22] Filed: Oct. 14, 1997

[51] Int. Cl.[6] ..... A01H 5/00

[52] U.S. Cl. ..... Plt./309

[58] Field of Search ..... Plt./87.1, 309

[56] References Cited

U.S. PATENT DOCUMENTS

| | | | |
|---|---|---|---|
| P.P. 8,261 | 6/1993 | van Andel | Plt./87.1 |
| P.P. 8,698 | 4/1994 | de Jong | Plt./87.1 |
| P.P. 9,100 | 4/1995 | van Andel | Plt./87.1 |

OTHER PUBLICATIONS

UPOV–ROM, 1998/01, Plant Variety Database, GTI Jouve Retrieval Software, citation for 'Testapink'.

*Primary Examiner*—Howard J. Locker
*Attorney, Agent, or Firm*—Christie, Parker & Hale, LLP

[57] ABSTRACT

A new and distinct Alstroemeria plant variety producing flowers of good quality and attractive coloration.

1 Drawing Sheet

BACKGROUND OF THE INVENTION

The present invention relates to a new and distinct variety of Alstroemeria which was discovered as a natural occurring whole plant mutation of the variety 'Stamond' (U.S. Plant Pat. No. 9,100). The varietal denomination of the new variety is 'Testapink'.

The first act of asexual reproduction of 'Testapink' was in Aalsmeer, The Netherlands, by propagation by dividing rootstocks. Asexual reproduction by dividing rootstocks through successive generations in Aalsmeer, The Netherlands, has demonstrated that the combination of characteristics as herein disclosed for 'Testapink' are firmly fixed and retained through successive generations.

'Testapink' has not been observed under all possible environmental conditions. Phenotypic expression may vary with variations in environment such as temperature, light intensity, day length and growing and cultural conditions.

SUMMARY OF THE INVENTION

The new variety of Alstroemeria, 'Testapink', produces flowers characterized by unusual coloration, as described herein, and good quality.

DESCRIPTION OF ILLUSTRATION

The new variety of Alstroemeria hybrid is illustrated in the accompanying illustration, which shows typical flower characteristics, with colors being as nearly true as is possible for illustrations of this type.

DETAILED DESCRIPTION OF THE NEW VARIETY

The following is a detailed description of the new cultivar of Alstroemeria hybrid as observed in a greenhouse in Aalsmeer, The Netherlands. Color designations indicated are in accordance with The Royal Horticultural Society Colour Chart by color plate designations.

Botanical classification:
- *Family*.—Amaryllidaceae.
- *Genus*.—Alstroemeria sp.
- *Commercial*.—Alstroemeria hybrid.

Origin: Sport.

Plant:
- *Form*.—Bush.
- *Shape*.—Upright.
- *Height*.—About 150 to 250 cm.
- *Internode length*.—About 1 to 8 cm.
- *Growth rate*.—Fast; the length of time (number of days) taken from young plants (rooted rootstocks, the stage of development in which the varieties are sold) to flowering stage under commercial greenhouse conditions is about 80–90 days.
- *Main stem or cane length*.—About 200 cm, pinching not required.
- *Growth*.—Vigorous.
- *Strength*.—Strong.

Foliage:
- *Quantity*.—Abundant.
- *Number of leaves*.—About 35 to 45.
- *Size of leaf*.—Length: About 15 to 20 cm. Width: About 3 to 5 cm.
- *Shape of leaf*.—Elliptical.
- *Margin type*.—Straight.
- *Texture*.—Glossy.
- *Color*.—Upper side: Near 137A. Underside: Near 137C.
- *Rhizomes*.—Yes. Color: Near 155D. Size: About 10 to 30 cm in length.

Inflorescence—Flower/floret:
- *Blooming habit*.—Continuous; Spent umbels not required to be pinched to maintain the plant in a continuous blooming condition.
- *Blooms*.—Profusely. Spring: Yes. Fall: Yes.
- *Size (when first anthers release pollen)*.—Diameter: About 7 cm. Depth: About 5 cm.
- *Borne*.—Singly.
- *Shape or form*.—When bloom first opens: Cup. When bloom matures: Cup.
- *Fragrance*.—None.
- *Lasting quality*.—On plant: About 4 weeks. As cut flower: About 20 to 26 days.
- *Tepalage*.—Number of tepals: 6. Arrangement: 2 concentric circles of 3 tepals. Form: Obovate. Margin type: Minutely crimped. Apex: Pointed. Texture: Soft. Appearance: Velvety.

*Color*.—Outer tepal: Body near 62B/155D; base near 155D; side near 62B/155D. Inside tepal: Body near 4D/62B; base near 155D; side near 62B/155D. Color summary: Outer tepal: Near 62B/155D. Base: Near 155D. Reverse side: Near 62B/155D. Inside tepal: Near 4D/62B. Base: Near 155D. Reverse side: Near 62B/155D. Two inner lateral tepals: 20–40 spots, near 185A. Inner median tepal: 0–15 spots, near 185A. Three outer tepals: 1–2 spots, near 185A; greenish coloration of tepal tips near 131C.

*Peduncle or flower stem*.—Length: About 5 to 8 cm. Color: Near 137b. Strength: Strong. Upright: Yes. Discoloration after full bloom: No. Is bloom affected by wet or hot weather: No.

*Persistence*.—No, flower does not hang on and dry.

*Disease resistance*.—Typical of alstroemeria.

Bud:

*Size*.—Diameter: About 1 to 2 cm. Depth or length: About 2 to 4 cm.

*Form or shape*.—Pear-shaped, long, pointed.

*Rate of opening*.—Fast.

*Color of tepals*.—When tepals begin to unfurl: Near 62B.155D. When tepals first divide: Near 62B/155D.

*Peduncle or flower stem*.—Length: About 5 to 8 cm. Hairy: No.

*Strength or character*.—Erect.

*Color*.—Near 137B.

Reproductive organs:

*Stamen*.—Number 6. Arrangement: Around the style, side-by-side.

*Anthers*.—Size: About 8 to 10 mm. Color: Near 161A.

*Filaments*.—Length: About 5 cm. Color: Near 62B.

*Pollen*.—Color: Near 161A.

*Pistils*.—1.

*Styles*.—Length: About 4 to 5 cm. Color: Near 62B.

*Stigmas*.—Color: Near 62B.

Fruit:

*Fertile*.—Yes.

*Shape*.—Round.

*Color at maturity*.—Near 163A.

I claim:

1. A new variety of Alstroemeria plant substantially as herein shown and described.

* * * * *

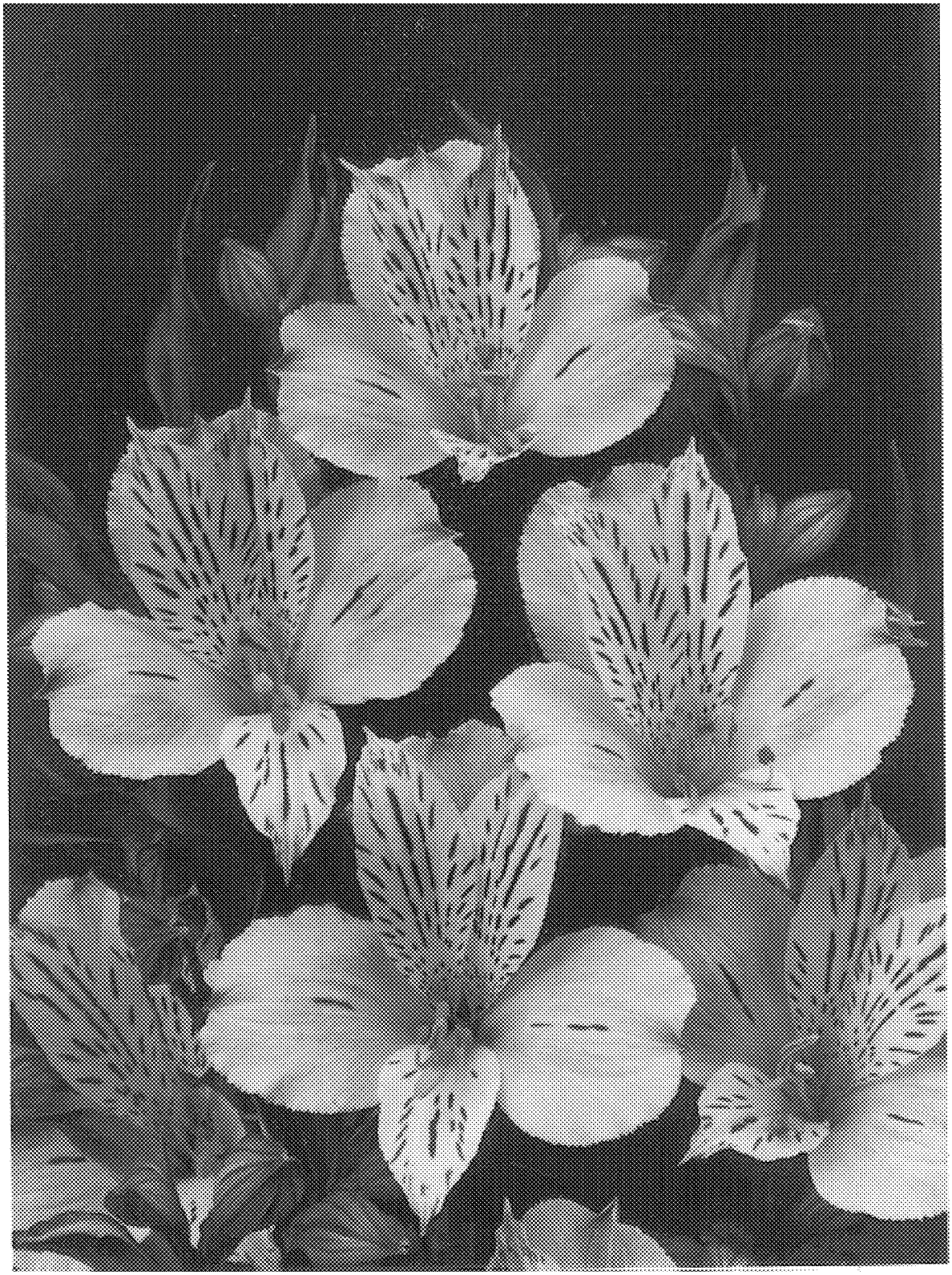

UNITED STATES PATENT AND TRADEMARK OFFICE

CERTIFICATE OF CORRECTION

PATENT NO. : Plant 10,900
DATED : May 18, 1999
INVENTOR(S) : Jacob van Andel

It is certified that error appears in the above-identified patent and that said Letters Patent is hereby corrected as shown below:

Column 3, line 12, replace "Near 137b" with --Near 137B--.
Column 3, line 23, replace "62B.155D" with --62B/155D--.

Signed and Sealed this

Twenty-seventh Day of March, 2001

*Attest:*

Nicholas P. Godici

NICHOLAS P. GODICI

*Attesting Officer*

*Acting Director of the United States Patent and Trademark Office*